(12) United States Patent
Schwarz et al.

(10) Patent No.: US 12,246,087 B2
(45) Date of Patent: Mar. 11, 2025

(54) COMPOSITION FOR INTRAORAL DELIVERY OF BIOLOGICALLY ACTIVE PEPTIDES AND PROTEINS

(71) Applicant: PHARCON INC., Toronto (CA)

(72) Inventors: Joseph Schwarz, Toronto (CA); Michael Weisspapir, Toronto (CA)

( * ) Notice: Subject to any disclaimer, the term of this patent is extended or adjusted under 35 U.S.C. 154(b) by 345 days.

(21) Appl. No.: 15/768,758

(22) PCT Filed: Oct. 14, 2016

(86) PCT No.: PCT/IB2016/002013
§ 371 (c)(1),
(2) Date: Apr. 16, 2018

(87) PCT Pub. No.: WO2017/093810
PCT Pub. Date: Jun. 8, 2017

(65) Prior Publication Data
US 2018/0311146 A1 Nov. 1, 2018

Related U.S. Application Data

(60) Provisional application No. 62/241,327, filed on Oct. 14, 2015.

(51) Int. Cl.
| | |
|---|---|
| *A61K 9/00* | (2006.01) |
| *A61K 9/107* | (2006.01) |
| *A61K 9/20* | (2006.01) |
| *A61K 38/19* | (2006.01) |
| *A61K 38/20* | (2006.01) |
| *A61K 38/22* | (2006.01) |
| *A61K 38/28* | (2006.01) |
| *A61K 47/10* | (2017.01) |
| *A61K 47/14* | (2017.01) |
| *A61K 47/24* | (2006.01) |
| *A61K 47/22* | (2006.01) |
| *A61K 47/28* | (2006.01) |

(52) U.S. Cl.
CPC ............ *A61K 9/006* (2013.01); *A61K 9/0095* (2013.01); *A61K 9/107* (2013.01); *A61K 9/2013* (2013.01); *A61K 38/19* (2013.01); *A61K 38/20* (2013.01); *A61K 38/22* (2013.01); *A61K 38/28* (2013.01); *A61K 47/10* (2013.01); *A61K 47/14* (2013.01); *A61K 47/24* (2013.01); *A61K 47/22* (2013.01); *A61K 47/28* (2013.01)

(58) Field of Classification Search
None
See application file for complete search history.

(56) References Cited

U.S. PATENT DOCUMENTS

| | | | | |
|---|---|---|---|---|
| 6,638,522 | B1 * | 10/2003 | Mulye | A61P 31/00 424/439 |
| 8,475,832 | B2 * | 7/2013 | Myers | A61P 25/36 424/435 |
| 9,675,550 | B2 * | 6/2017 | Croyle | A61K 39/12 |
| 2010/0113376 | A1 * | 5/2010 | Schwarz | A61K 9/1075 514/29 |
| 2015/0250856 | A1 * | 9/2015 | Schwarz | A61K 9/2018 514/5.9 |

FOREIGN PATENT DOCUMENTS

| | | | |
|---|---|---|---|
| EP | 1510206 A1 | | 3/2005 |
| WO | WO 01/22937 | * | 4/2001 |
| WO | 2015132660 A1 | | 9/2015 |
| WO | 2017/093810 A2 | | 6/2017 |

OTHER PUBLICATIONS

Driver et al. (American Journal of Physiology, 132 (1)281-292, 1941). Factors in the absorption of insulin . . . .*
Karamanidou et al. (European Journal of Pharmaceutics and Biopharmaceutics 97 (2015) 223-229, Available online Apr. 29, 2015) Self-nanoemulsifying drug delivery systems for oral insulin delivery . . . .*
International Search Report of PCT/IB2016/002013 mailed on Jul. 20, 2017 (3 pages).
Written Opinion of PCT/IB2016/002013 mailed on Jul. 20, 2017 (3 pages).
Ping Li et al, "Self-nanoemulsifying drug delivery systems for oral insulin delivery: In vitro and in vivo evaluations of enteric coating and drug loading", International Journal of Pharmaceutics, (2014), vol. 477, pp. 390-398.
M.R. Rekha et al, "Oral delivery of therapeutic protein/peptide for diabetes—Future perspectives", International Journal of Pharmaceutics, (2013), vol. 440, pp. 48-62.
Supplementary European Search Report of EP 16870057 dated Apr. 24, 2019 (2 pages).
European search opinion of EP 16870057 (4 pages).
Senel, S., et al., "Delivery of Bioactive Peptides and Proteins Across Oral (Buccal) Mucosa"; Current Pharmaceutical Biotechnology, 2001, 2, pp. 175-186.
El-Kattan, A., et al., "Oral Absorption, Intestinal Metabolism and Human Oral Bioavailability" Pharmacokinetics, Dynamics and Metabolism Department, Pfizer Inc., USA; 2012. DOI: 10.5772/31087 (https://www.intechopen.com/chapters/29240).
Maher et al., Intestinal Permeation Enhancers for Oral Peptide Delivery, Advanced Drug Delivery Reviews (2016) doi: 10.1016/j.addr.2016.06.005.
FDA Inactive Ingredient Database; https://www.accessdata.fda.gov/scripts/cder/iig/index.cfm (accessed on May 16, 2022).
Oostendorp R. L., et al. "Paclitaxel in self-micro emulsifying formulations: oral bioavailability study in mice" Invest. New Drugs (2011) 29:768-776.
Aungst et al, "Site Dependence of Absorption Promoting Actions of Laureth-9, Na Salicylate, Na2EDTA, and Aprotinin on Rectal, Nasal and Buccal Insulin Delivery", Pharmaceutical Research, vol. 5, No. 5, 1988, pp. 305-308.

(Continued)

*Primary Examiner* — Tigabu Kassa
(74) *Attorney, Agent, or Firm* — Mayer Brown LLP (57) ABSTRACT

The present disclosure relates to self-emulsifying pharmaceutical compositions for transmucosal delivery of biologically active peptides and proteins.

7 Claims, 4 Drawing Sheets

(56) References Cited

OTHER PUBLICATIONS

Berberian, D.A., et al, "The toxicology and biological properties of laureth 9 (a polyoxyethylene lauryl ether), a new spermicidal agent," Toxicology and Applied Pharmacology, vol. 7, Issue 2, 1965, pp. 206-214 (abstract only).

Aungst et al., "Comparison of the effects of various transmucosal absorption promoters on buccal insulin delivery," International Journal of Pharmaceutics, 1989, 53: 227-235.

Maher et al. "Formulation strategies to improve oral peptide delivery"; Pharm. Pat. Anal. (2014) 3(3), 313-336.

Chun-Ying Cui et al., "Sublingual Delivery of Insulin: Effects of Enhancers on the Mucosal Lipid Fluidity and Protein Conformation, Transport, and in Vivo Hypoglycemic Activity" Biol. Pharm. Bull. (2005) 28(12) pp. 2279-2288.

Zhou Y. et al, "Effect of Salicylate on the Elasticity, Bending Stiffness, and Strength of SOPC Membranes," Biophysical Journal, vol. 89, 2005, 1789-1801.

Sara Miles, "Methyl Salicylate," xPharm: The Comprehensive Pharmacology Reference, Elsevier, 2007, pp. 1-6.

Lugassy D.M. , "39:Salicylates" pp. 1-34.

Risk Profile Methyl Salicylate , Oct. 12, 2012.

Summary of Evaluations Performed by the Joint FAO/WHO Expert Committee on Food Additives, dated Jan. 29, 2003.

I. Nardin, S. Köllner, "Successful development of oral SEDDS: Screening of excipients from the industrial point of view" https://doi.org/10.1016/j.addr.2018.10.014, Adr (2018).

Malingré, MM et al., "The co-solvent Cremophor EL limits absorption of orally administered paclitaxel in cancer patients" British Journal of Cancer (2001), p. 1472-1477.

Bergfeld, Wilma F. et al., M.D., F.A.C.P. et al., "Amended Safety Assessment of Salicylic Acid and Salicylates as Used in Cosmetics", The 2019 Cosmetic Ingredient Review Expert Panel (2019).

Wolowich, William R. et al., "Plasma Salicylate from Methyl Salicylate Cream Compared to Oil of Wintergreen", Marcel Dekker, Inc. (2003), p. 355-358.

Bernauer, Dr U. et al., "Opinion on Methyl salicylate", Scientific Committee on Consumer Safety (2021).

\* cited by examiner

COMPOSITION FOR INTRAORAL DELIVERY OF BIOLOGICALLY ACTIVE PEPTIDES AND PROTEINS

CROSS REFERENCE TO RELATED APPLICATION

This application is a national stage entry of International Application No. PCT/IB2016/002013, filed on Oct. 14, 2016, which claims benefit of U.S. Provisional Patent Application No. 62/241,327 filed on Oct. 14, 2015; which are incorporated herein by reference in their entirety to the full extent permitted by law.

BACKGROUND OF INVENTION

Most of the therapeutically active peptides and proteins are delivered parenterally, i.e., by subcutaneous, intramuscular or intravenous routes, which is invasive, traumatic, usually painful and inconvenient. Administration of biologically active peptides and proteins is limited to injection due to fast enzymatic degradation of the peptides in gastrointestinal tract after oral administration (pepsin is stomach, trypsin, chymotrypsin, carboxypeptidases and other enzymes in the intestine) and poor and erratic absorption of large molecules of polypeptides through intestinal mucosa. This resulting in a substantial loss of activity and low bioavailability.

Nasal administration of peptides currently is limited by delivery of short peptide hormones, such as vasopressin and oxytocin, still with low bioavailability.

It is obvious that demand for development of peptide and protein formulations for less invasive routes of administration such as oral, transmucosal, or transdermal remains high. Transmucosal delivery through absorptive mucous membranes such as oral, buccal, sublingual, eye, nasal, pulmonary, rectal, and vaginal membranes, on the other hand, has the advantage of being noninvasive and of bypassing hepato/gastrointestinal clearance (at least initially). Peptides and proteins, however, are generally not well absorbed even through mucosae because of their molecular size and hydrophilic character. In general, enzyme inhibitors and absorption enhancers need to be co-administered for successful transmucosal delivery of bioactive peptides and proteins.

Non-parenteral dosage forms for biologically active peptides, especially insulin, are of big demand. Among different non-injectable delivery methods of insulin oral administration of this peptide is one of the most promising. Despite tremendous efforts very few products are marketed or have reach late stages or development. Due to peptide nature insulin molecule in oral formulations must be protected from enzymatic degradation in the gastro-intestinal tract. It requires incorporation of protease inhibitors into formulations, and extended use of such inhibitors may cause serious side effects.

Inhalable insulin formulation (e.g., Exubera® and Afrezza®) did not seize the significant market part. Oral sprays (e.g., Ora-Lyn™) require multiple administrations and an expensive and complex delivery device. Intranasal way for peptide delivery has limitations due to often irritation and sensitization. [Lutz Heinemann, Yves Jacques, "Oral Insulin and Buccal Insulin: A Critical Reappraisal" J. Diabetes Sci. Technol. 2009; vol. 3, No 3, pp. 568-584]. [Sandra Soares, "Novel non-invasive methods of insulin delivery" Expert Opin. Drug Deliv. 2012; vol. 9, No. 12, pp. 1539-1558].

Intraoral route of delivery of different peptides attracted tremendous attention in the last decades. Oral mucosa has good potential as an excellent place for enhanced delivery of various drugs, including peptides.

Buccal and sublingual mucosa is relatively easy penetrable for small, especially hydrophobic, molecules (below 500 Dalton). In order to overcome penetration resistance of mucosa to large hydrophilic peptide molecules, various approaches have been exploited: penetration enhancers such as polar solvents—liquid PEGs, Propylene glycol, DMSO, N-Methylpyrrolidone; lipid disturbants-Azone®, Decylmethylsulfoxide; non-ionic surfactants—polysorbates, poloxamers, alkyl glucosides and other sugar esters; anionic surfactants—sodium lauryl sulfate (SLS), salts of fatty acid; phospholipids—lecithin, phosphatidylcholines, other phospholipids; bile acids—sodium cholate, desoxycholate, taurocholate and analogs; high concentrations of terpenes—menthol, borneol, eucalyptol; chelators—EDTA, citric acid, etc.; lipids and esters—mono-, di- and triglycerides, glycol esters, various cyclodextrines and other compounds. [Kinesh V. P. et al, "Novel Approaches for Oral Delivery of Insulin and Current Status of. Oral Insulin Products". International Journal of Pharmaceutical Sciences and Nanotechnology, 2010, Vol. 3, No 3, pp. 1057-1064].

The influence of various penetration enhancers on the membrane fluidity and insulin delivery "in vitro" and "in vivo" was investigated in article of Cui et al. [Cui C. Y. et al., "Sublingual delivery of insulin: effects of enhancers on the mucosal lipid fluidity and protein conformation, transport, and in vivo hypoglycemic activity". Biol. Pharm. Bull. 2005, Vol. 28, No. 12, pp. 2279-88]. The enhancing effects may be due to one or multiple factors: increasing the mucosal lipid fluidity, directly loosing the tight junction of epithelia, and other parameters. The purposes of this study were to evaluate effects of enhancers on the mucosal lipid fluidity and protein conformation, transport, and hypoglycemic activity in normal rats. The effects on sublingual mucosa, and aggregation states of insulin were estimated using fluorescence polarization, and circular dichroism method, respectively. The human immortalized oral epithelial cell monolayer was used for evaluating transport of insulin. Hydroxylpropyl-beta-cyclodextrin (HP-beta-CD), chitosan, polyethylene-polypropylene glycol, polyoxyethylene lauryl ether, polysorbate 80, egg lecithin and oleic acid, were used as a penetration enhancers. Formulations, described in this article, contain high levels of the enhancers—5 to 10 percent of the liquid composition.

Aungst B. J. et al. tested efficacy of various penetration adjuvants, including non-ionic surfactants, bile salts, fatty acids, enzymes, polar solvents and their combinations on buccal insulin delivery in high concentration. [Aungst B. J., et al., "Comparison of the effects of various transmucosal absorption promoters on buccal insulin delivery" International Journal of Pharmaceutics, 1989, vol. 53, pp. 227-235]. It was found that most of such adjuvants are effective only when used at high (5-10%) concentrations.

In order to improve bioavailability of transmucosally delivered peptides they could be incorporated into nanoparticles, micro- and nanoemulsions, micellar solutions or self-emulsifying compositions. Various solid, semi-solid and liquid dosage forms as well as pressurized sprays, buccal films and patches were proposed for intraoral administering of peptides. [Hui-Bi xu et al., "Hypoglycaemic effect of a novel insulin buccal formulation on rabbits" Pharmacological Research, 2002, Vol. 46, No. 5, pp. 459-467]. [Amani Elsayed et al., "Formulation and characterization of an oily-based system for oral delivery of insulin" Eur. J. Pharm. Biopharm. 2009, vol. 73, pp. 269-279]. [Bruno Sarmento et al., "Oral insulin delivery by means of solid lipid nanoparticles" Inter. J. Nanomed. 2007 vol. 2, No 4, pp. 743-749].

U.S. Pat. No. 5,516,523A describes transmucosal administration of peptides and proteins in presence of buffered catonic polyaminoacids as penetration enhancers. U.S. Pat. No. 5,766,620A proposes use of cell envelope disordering compounds such as solvents, steroidal detergents, bile salts, chelators, surfactants, non-surfactants, fatty acids as permeation enhancers for buccal delivery of glucagon-like insulinotropic peptides in adhesive patch or tablet.

Conjugates of peptide and protein with covalently attached water soluble polymers, polyalkylene oxides, were used for enhanced transmucosal delivery according WO 2006135930 A2.

In application WO 1994003157 A1 a composition for transmucosal or transdermal delivery of peptides, based on peptide incorporation into multiphase system based on water and lipid phases such as liposomes or microemulsions, and polymer for viscosity modifying of the formulation are described.

WO 2011004395 A1 shows use of microemulsion formulation for delivery of biologicals, based on combination of a fatty acid derivative of glycerol, low HLB and high HLB surfactants, co-solvent and stabilizing buffer with some additives U.S. Pat. No. 5,514,670A is devoted to oil-in water submicron emulsions, containing biologically active peptide, where oil droplets of the emulsion are coated with mucoadhesive polymer to improve transport of the peptide.

Microemulsion composition with increased viscosity for protein and peptide delivery via buccal, nasal, vaginal or rectal described in U.S. Pat. No. 5,759,566A.

Oral administration of peptide hormone calcitonin with assistance of penetration enhancers such as N-(5-chlorosalicyloyl)-8-aminocaprylic acid, N-(10-[2-hydroxybenzoyl] aminodecanoic acid and N-(8-[2-hydroxybenzoyl]amino) caprylic acid US described in U.S. Pat. Nos. 7,569,539 B2 and 8,410,052 B2.

Another system for calcitonin delivery based on pH dependent composition and surfactant in enteric coated dosage form presented in U.S. Pat. No. 5,912,014A.

Non-ionic (polysorbates, poyethoxylated ethers and esters, PEG and PPO block copolymers) and anionic surfactants, such as salt forms of alkyl sulfates (sodium lauryl sulfate), bile acids and steroid derivatives (cholates, deoxycholates, taurocholates), salts of (aryl)aminocaprylic acids usually are added to delivery systems in high amounts and cause solubilization and disruption of cell membranes, enhancing penetration of large molecules.

U.S. Pat. No. 6,290,987 discloses a mixed liposomal formulation containing alkylsulfate salts delivered intraorally as a spray. U.S. Pat. No. 6,350,458 denotes use of mixed micelles for transbuccal delivery of insulin. Proposed oral spray compositions contain high concentration of alkylsulfates, such as sodium lauryl sulfate, possessing high irritation potential for oral mucosa.

U.S. Pat. No. 6,635,617 is related to pulmonary delivery of Insulin in combination with menthol, using bronchodilatory properties of this terpene. U.S. Pat. No. 7,112,561 describes use of macrocyclic penetration enhancers in nasal formulations for insulin emulsions in acidic conditions.

U.S. Pat. No. 4,579,730 describes cholate complexes of insulin with protease inhibitors for oral delivery. Use of various complexes and biodegradable nanoparticles with sodium deoxycholate as ion-pair reagent for enhancement of Insulin delivery is described in [Sun at al. "Hydrophobic ion pairing of an insulin-sodium deoxycholate complex for oral delivery of insulin" Int. J. Nanomed. 2011, vol. 6, pp. 3049-3056].

Patent application WO 2011/086093 describes liquid self-nanoemulsifying systems for oral delivery of acylated derivatives of Insulin, based on combination of polar solvent and non-ionic surfactants.

US Patent application 2009/0274758 A1 describes solid composition for intraoral delivery of different types of biologically active molecules, including Insulin, using hydrophilic polymeric matrixes or liquid formulations, containing liposomes or pro-liposomal combinations together with menthol as a penetration enhancer and sodium lauryl sulfate (SLS) and other anionic surfactants. Due to proposed very high concentrations of SLS and menthol such formulations should possess serious local irritation potential.

In patent application WO 2012/104834 A1 a buccal bioadhesive polymeric film loaded with insulin and penetration enhancers is described.

Patent application WO 2005/089722 A1 describes use of Insulin combination with chelators such as EDTA and citric acid, preventing Insulin aggregation into hexamers, given sublingually.

Various penetration enhancers were proposed for increasing of transmucosal transportation of peptides and proteins: polar solvents (PG, DMSO); terpenes (menthol, borneol); surfactants (Brij, SLS). US Patent application 2004/0258623 describes oral spray containing Insulin, lecithin, polar solvent and borneol as penetration enhancers.

Menthol is described as effective transbuccal penetration enhancer [Amir H. Shojaei et al., "Transbuccal permeation of a nucleoside analog, dideoxycytidine: effects of menthol as a permeation enhancer" Int. J. Pharm. 1999, vol. 192, pp. 139-146].

Significant improvement of transdermal or transmucosal penetration for polar compounds can be achieved by applying high concentrations of such enhancers. In most cases it associated with serious local irritation, especially for intranasal route of administration. Tissue damage and delipidization, loss of taste and odor sense may be caused by administration of formulations with high concentration of penetration enhancers.

Various microemulsions and nanoemulsions, especially in self-emulsifying pre-concentrates, were widely investigated as delivery systems for oral delivery of peptides, including insulin. Spontaneously formed colloidal dispersions are absorbed in gastro-intestinal tract and in some cases could increase efficacy of drug absorption. As described in patent application WO 2011/086093, combination of insulin and polar organic solvent with low content of lipids and elevated concentration of surfactants with high HLB, administered into duodenum or distant parts of intestine, improved insulin delivery via gastro-intestinal tract.

Bioadhesive gels with insulin, surfactants and bile acid derivatives for buccal and sublingual delivery presented in the article of [N. Das et al., "Development and in vitro evaluation of insulin-loaded buccal Pluronic F-127 gels", Pharmaceutical Development and Technology, 2010 vol. 15(2) pp. 192-208].

Bioadhesive sublingual tablets containing chitosan and various biologically active compounds, including insulin and sildenafil, described in patent application WO 2010/118516 A1.

U.S. Pat. No. 8,241,670 B2 describes composition for facilitating penetration of peptides across a biological barrier and comprising of lyophilized peptide, suspended in the oil phase containing salts of a medium chain fatty acid and additionally a non-ionic surfactant. Such formulations allowed to deliver octreotide via oral route in enteric coated capsules, where 20 mg of oral peptide is close by efficacy to 0.1 mg in subcutaneous injection [S. Tuvia, et al., "Oral Octreotide Absorption in Human Subjects: Comparable Pharmacokinetics to Parenteral Octreotide and Effective Growth Hormone Suppression" J. Clin. Endocrinol. Metab. 2012 vol. 97 pp. 2362-2369].

Incorporation of peptides and proteins into colloidal delivery systems, such as nanoparticles, nano- and microemulsions or liposomes, may improve drug transportation, but due to high water solubility of the protein efficacy of drug incorporation remains low. It can be improved by covalent modification of the peptides with hydrophobic moieties (e.g., acylation with long chain fatty acids—conjugate with myristoyl (as for insulin Detemir), hexadecyl- or octadecyl blocks (see US Pat Appl. 20140255481). As another approach, an addition of appropriate bulky lipophilic counter-ions to increasing hydrophobicity of proteins and peptides, also can be evolved.

U.S. Pat. No. 7,674,767 is devoted to lipid nanoparticles loaded with water-soluble peptide or protein drugs for oral administration by using of peptide complexes with help of polymers and surfactants. Surfactant content in the formulations is high (30-80% by weight), and any visible efficacy was obtained for insulin loaded systems at very big doses (20 IU/kg and more).

U.S. Pat. No. 8,586,103 describes sustained release composition containing liquid solution with ionic complexes, including complexes of lysozyme (MW~18,000), octreotide (MW ~1019) and leuprolide (MW ~1209) with sodium dioctylsulfosuccinate (docusate), lauryl sulfate (SLS), oleate and other anionic compounds. The composition comprises suspension or solution of such complexes in a hydrophobic vehicle and designed for parenteral sustained release delivery.

US Patent application 20130345134 A1 describes solid compositions comprising a salt of N-8-(2-hydroxybenzoyl) aminocaprylic acid as a penetration enhancer in solid dosage forms for oral delivery of a GLP-1 agonists.

Nevertheless despite numerous attempts the need in development of non-invasive delivery system for insulin and other peptides is still unmet and compels development of stable convenient intra-oral dosage forms for biologically active peptides and proteins.

SUMMARY OF THE INVENTION

The present invention relates to intraoral solid pharmaceutical compositions for sublingual or buccal administration, containing a biologically active peptide, such as insulin or insulin analogs, glucagon-like peptide and analogs (e.g., GLP-1, exenatide, liraglutide), calcitonin, oxytocin, vasopressin, octreotide, leuprolide, gosereline, enkephalins, endorphins, interferons, interleukins, integrilin, parathyroid hormone agonists and antagonists (e.g., Tiraparatide, Eptifibatide), natriuretic hormone (Nesiritide), growth factors, necrosis factors, etc. The object of the invention is to provide safe and convenient method for transmucosal delivery of biologically active peptide, providing fast onset of biological action.

In one aspect the invention provides effective transmucosal delivery of biologically active polypeptide, by sublingual administration of solid dosage form, comprising the peptide or protein and hydrophobic counter-ion, negatively charged at physiological pH.

In another aspect of the invention, biologically active peptide and counter-ion incorporated into a self-emulsifying composition, forming oil-in-water emulsion In another aspect of the invention, the emulsion is formed spontaneously after contact of the dosage form with saliva or wet mucosal surface or body fluid, such as gastric or intestinal fluid.

In another yet aspect of the invention, droplet size of the formed oil-in-water emulsion is smaller than 1 micrometer, usually the droplets size is between 2-200 nm.

In another aspect of the invention, the salt or complex between the peptide and the counter-ion in completely dissolved in the self-emulsifying composition.

In another yet aspect of the invention, the salt of complex of the counter-ion and the peptide remains completely dissolved in the oil phase of the formed droplets of the spontaneously formed oil-in-water emulsion.

In another aspect of the invention the oil phase is liquid at body temperature and comprises of physiologically acceptable compounds, such as edible oils, mono-, di- and triglycerides, essential oils, tocopherols, tocotrienols, aliphatic and aromatic esters of fatty acids, cyclic alcohols, sterols, phenolic compounds and organic acids. The main feature of the oil phase is an ability to provide the complete solubilization of the peptide in the oil phase during storage and in the core of emulsion droplets after self-emulsifying.

In another yet aspect of the invention, the mixture of physiologically acceptable surfactants contains aromatic non-ionic surfactant, selected from the group of Tocophersolan, polyethoxylated cholesteryl, polyethoxylated lanolin, Triton X-100 and Tyloxapol.

It was surprisingly found that complete solubilization of the hydrophobic peptide-counter ion complex into hydrophobic core of emulsion droplets, simultaneously formed after contact of the composition with the body fluids, noticeably enhances transmucosal penetration of biologically active protein or peptide, such as insulin, insulin analogs or other peptides and proteins. The process can be caused by combination of high infiltration rate of tiny oil droplets. Incorporation of hydrophobic complexes of protein or peptide into self-emulsifying formulation in accordance with the invention improves its penetration in higher extent than similar emulsions without wherein the complete solubilization is not achieved. Moreover, complete solubilization of the peptide complexes in the oil phase prevents loss of biological activity of the peptide during the storage of the product.

Non-limiting examples of counter ions are diacylphosphatidylglycerol derivatives such as dimyristoyl-, dioleyl-, dipalmitoyl- and distearoyl phosphatidylglycerols, -tocopheryl succinate, tocopheryl phosphate, sodium dioctylsulfosuccinate, mono- and disubstituted cetylphosphates, cholates, deoxycholates, ammonium glycyrrhizinate, cholesteryl hemisuccinate, cholesteryl sulfate, and cholesteryl sulfate.

By another aspect of the invention the peptide or protein molecule is associated with oil droplets of the formed emulsion with help of hydrophobic counter ion. Used counter-ions associate with polypeptide molecule and increase their hydrophobization and association with hydrophobic core part of nanoemulsion, containing appropriate solubilizing compound, such as esters of salicylic acid. Various formulations were obtained with diacylphosphatidylglycerol derivatives, tocopheryl acid succinate, cholates, deoxycholates, cholesteryl sulfate, dicetyl phosphate used as hydrophobic counter-ions.

The dosage form for intraoral transmucosal delivery of insulin and other peptides may be a compressed tablet. Additionally the tablet can comprise non-ionic surfactants, fillers, such as pharmaceutical grade polyols or sugars (e.g., sucrose, sorbitol, mannitol, erythritol), binders (Polyvinylpyrrolidone, cellulose esters, polyethylene glycols), disintegrants (cross-carmellose, cross-povidone) preservatives (e.g., parabens, sorbic acid, benzoic acid and pharmaceutically acceptable salts thereof), lubricants, glidants, flavors, antioxidants, etc. These components are incorporated into tablet matrix, prepared by granulation, blending and compression. According to the invention, the compressed sublingual tablet contains insulin in combination with surfactant, hydrophobic solubilizing oil phase mixture, counter-ion and chelating agent, spontaneously forms a nanoemulsion on contact with saliva.

Tablet matrix granulate, containing insulin and other excipients and suitable for compression, could be prepared by wet granulation, compaction, trituration or dry blending. Tablets were compressed into round, oval or other required shape tablets using appropriate tablet press.

By another aspect of the invention, the solid dosage form for sublingual administration of peptides and proteins should dissolve in the mouth in 3-30 minutes.

In yet another aspect of the invention, the biologically active peptide or protein may be incorporated into a liquid composition, comprising said peptide, counter-ion, solubilizing oil phase components and additionally physiologically acceptable excipients, such as sweeteners, solvents, cosolvents, vitamins, penetration enhancers, antioxidants, antibacterial preservatives, stabilizers and flavors.

By another aspect of the invention, the liquid dosage form can be prepared as a solution for oral, intraoral or buccal administration and may be dispensed and administered using pressurized spray device, non-pressurized spray device, metered dose pump, syringe, pipette, dropper, spoon or single dose unit such as liquid filled capsules or softgel capsules.

In a preferred embodiment of the invention a dosage form (compress tablet or liquid self-emulsifying concentrate) for transmucosal administration may comprises 0.0001 to 10 mg of peptide or protein per delivered unit (tablet, capsule, lozenge, drop, spray, puff or otherwise delivered amount)

DETAILED DESCRIPTION OF THE INVENTION

The transportation of a polar hydrophilic polypeptide or protein molecule through mucosal membrane can be alleviated by decrease of the resistance of mucosal tissues to drug diffusion. The oral mucosa can be subdivided according to the major regions in the oral cavity, a so-called non-keratinized area consisting of the floor of the mouth (sublingual), the buccal mucosa (cheeks), and a keratinized area comprising the gum (gingiva), the palatal mucosa, and the inner side of the lips. The rapid turnover of the epithelial cells relative to the skin is an important feature of the oral cavity that affects drug absorption by continually changing permeability characteristics.

The buccal epithelium is a non-keratinized squamous layer of cells, 500-600 mcm in thickness, composed of strata of different cell types with varying of maturity. The upper most superficial region is comprised of flattened compact layers of differentiated cells, about 150 mm thick. The buccal epithelium is highly vascularized and the papillary contour of the basal region permits efficient vascularization of the cells. Hydration of the mucous membranes, due to the contact with saliva, may strongly facilitate drug permeation. However, the mucus layer is small relative to other barriers that peptides encounter during their passage through the buccal mucosa.

Oral mucosal tissue contains a large amount of extracellular material, which not only gives the epithelium its elasticity but is also thought to contribute to the permeability barrier. Regional differences in permeability are dependent upon epithelial thickness, the eventual presence of a keratinized epithelium and the organization of intercellular material extruded by membrane-coating granules in the upper layers of the epithelium. Buccal mucosa contains mostly polar lipids such as phospholipids, cholesterol sulfate and glycosylceramides. This may result in fluidity and may create micro domains with specific properties. The non-keratinized regions have higher permeability to water and hydrophilic compounds than keratinized areas. [F. Veuilleza, et al., "Factors and strategies for improving buccal absorption of peptides" Eur. J. Pharm. Biopharm. 2001, v. 51, pp. 93-109].

Two main pathways seem to be associated with peptide transport through membranous tissues: the intracellular (transcellular) pathway where peptides traverse the epithelium across the cells, and the intercellular pathway where peptides diffuse through the intercellular lipids. The transcellular route may involve permeation across the apical cell membrane, the intracellular space and the basolateral membrane either by passive transport (diffusion, pH, partition) or by active transport (facilitated and carrier-mediated diffusion, endocytosis). The transcellular permeability of a peptide is a complex function of various physicochemical properties including size, lipophilicity, hydrogen bond potential, charge and conformation. Small polar molecules penetrate buccal epithelium via the intracellular route. The drug transport via aqueous pores in the cell membranes of the epithelium is also possible for substances of low molar size.

The second route, available to substances of a wide range of molecular weight, is an intercellular (paracellular) route. Within the intercellular space, there probably exist at least 
two pathways, one is essentially a hydrophobic route through the lipidic bilayer, while the second is more hydrophilic and associated with the narrow aqueous regions adjacent to the polar head groups of the lipids. A consequence of these two pathways is that the substances having nearly equal solubility in water and oil, traverse using both routes. Peptides are presumed to permeate through the aqueous pathways, i.e. the paracellular and aqueous pore paths. Paracellular transport occurs between the epithelial cells by passive diffusion across the intercellular junctional complex of the epithelium. It has also known that the oral mucosae contain carrier-mediated (active) transportation systems for small molecules and short peptides. [F. Veuillez et al. Biopharmaceutics "Factors and strategies for improving buccal absorption of peptides". Eur. J. Pharm. Biopharm. 2001, v. 51, pp. 93-109].

According to current paradigm, penetration enhancers improve mucosal peptide absorption by changing mucus rheology, i.e., reducing the viscosity and elasticity of mucus layer, as well as by increasing membrane fluidity and hence facilitating transcellular transport.

Utilization of polar organic molecules (NMP, DMSO, DMA, Azone, terpenes, propylene glycol, etc.) as penetration enhancers associated with irritation of mucosa, local or systemic toxicity and unpleasant taste of many of such compounds. Also due to high solubility in water most of these compounds cannot be incorporated into lipophilic membranes and modify membrane fluidity. Moreover, some surfactants (sodium lauryl sulfate, sodium laurate, acyl glycosides, nonoxynol, Brij, alkaline salts of fatty acids and salicylic acid), used as penetration enhancers, may destruct cell membranes and cause irritation.

Non-surfactants, e.g., terpenes (menthol, borneol), can modify fluidity of mucosal lipids, but for this effect they need to be used in relatively high concentrations, causing irritation and unpleasant taste changes.

The onset of biological effect of peptides occurs faster with formulations containing or forming nanoemulsions with incorporated active molecules than with formulations having high concentrations of penetration enhancers and surfactants only.

Use of counter-ions such as SLS, medium and long chain fatty acids, bile acids and cholates has been described in numerous patents and articles. In some circumstances the bioavailability of the incorporated peptides was improved, but for the most cases the improvement is erratic and poorly reproducible. It may be associated with poor solubility of peptide complexes in most lipids.

It was unexpectedly found that incorporation of such polar hydrophobic aromatic component as salicylic acid ester in some ratios into lipid phase of the emulsion allows complete solubilization of peptide-counter-ion complex in the oil core and keeps it in dissolved state after formation of the oil-in-water emulsion. It not only significantly improves incorporation of the formed complex/salt into lipid phase of the colloidal delivery system, e.g., emulsion, nanoemulsion or micelles, but also noticeably increases drug transporting via biological barriers.

The lipid-soluble protein or peptide complex with hydrophobic counter-ion, reversibly (non-covalently) associated with the basic aminoacid(s) of the peptide chain, penetrates through mucosal layers remaining incorporated into internal area of the oil droplet, being protected from damage and degradation, and gradually releases the biologically active polypeptide inside the body tissues, providing fast and effective onset of physiological action.

Lack of solubility of peptide complexes in the self-emulsifying composition can cause precipitation and sedimentation and significant loss of activity during storage. More important, if the solubility of the peptide-counter-ion complex in the oil phase of the formed droplet does not allow complete drug solubilization, the efficacy of drug delivery through biological barriers is considerably diminished.

Most of the proposed emulsion based compositions for peptide delivery comprise of traditional lipid components, such as mono-, di- and triglycerides, phospholipids, aliphatic esters such as alkyl citrates, adipates, tartrates or sebacates, lipid-soluble vitamins (e.g., vitamin E), benzyl benzoate, etc. In some formulations hydrophobization of the peptides is based on interaction with counter-ions such as SLS, bile acids, fatty acids or dioctylsulfosuccinate. Nevertheless, most of the biologically active peptides and proteins are polar hydrophilic water soluble compounds and their solubility in the proposed oil phases is relatively low. Even being completely dissolved in a combination of the oil phase components with surfactants and appropriate solvents (e.g., U.S. Pat. No. 8,586,103) the hydrophobized peptide complexes showed strong tendency to precipitate from the formed emulsion after emulsification. Most of the lipid components do not permit to receive satisfactory solubility in the oil phase after emulsification.

We found that addition to a lipid phase a polar hydrophobic physiologically acceptable component, selected from the group of esters of salicylic acid extraordinarily increases solubility of the peptides in form of hydrophobic complexes in the oil phase and allows to keep the peptide in completely dissolved state for extended period of time, sufficient for peptide transportation through the biological barriers and providing of the pharmacological action.

Additionally, use of salicylates significantly improves physical stability of the peptide formulations during the storage, especially in refrigerated conditions, compared with various lipids, mono-, di- and triglycerides based compositions.

More important, the complete solubilization of the peptide-counter ion complex in the hydrophobic self-nanoemulsifying composition containing salicylates prevents drug crystallization and decrease or even total loss of biological activity by the incorporated peptides during storage either at room temperature or in a refrigerated environment.

I. DEFINITIONS

For convenience, before further description of the present teachings, certain terms employed in the specification, examples, and appended claims are collected here. These definitions should be read in light of the remainder of the disclosure and as understood by a person of ordinary skill in the art. Unless defined otherwise, all technical and scientific terms used herein have the same meaning as commonly understood by a person of ordinary skill in the art.

A. General Terms

The use of the terms "a," "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

The phrase "and/or," as used herein, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements).

As used herein, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of" "Consisting essentially of", when used in the claims, shall have its ordinary meaning as used in the field of patent law.

As used herein, the phrase "at least one" in reference to a list of one or more elements should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, all transitional phrases such as "comprising," "including," "carrying," "having," "containing," "involving," "holding," "associated," "associated with," and the like are to be understood to be open-ended, i.e. to mean including but not limited to.

The use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein.

B. Terms Related to Compositions of the Present Disclosure

"Lipid" refers to a fatty or waxy organic compound that is readily soluble in nonpolar solvent (e.g. ether) but not in polar solvent (e.g water). Its major biological functions involve energy storage, structural component of cell membrane, and cell signaling. Examples of lipids are waxes, monoglycerides, diglycerides, triglycerides (edible oils, fats), fat-soluble vitamins, sterols, cholesterol, and phospholipids.

As used herein, "insulin" includes native insulin, proinsulin, insulin prodrugs, insulin analog, insulin derivatives, recombinant insulin or insulin from any origin, or any acceptable form thereof, which have activity similar to native insulin.

"Buccal mucosa" includes the portion of the oral mucosa that lines the cheeks.

"Oral mucosa" includes the mucus membrane lining the inside of the mouth and consists of stratified squamous epithelium termed oral epithelium.

As used herein "penetration enhancer" refers to a compound or mixture of compounds that increase the permeation of one or more drugs through epithelial cells. A penetration enhancer increases systemic delivery of one or more drugs.

"Permeate" or "permeation" refers to movement of a substance into or through epithelial cells. Permeation through epithelial cells delivers the substance systemically. Permeation may occur through an intracellular or intercellular pathway by either active or passive transport.

A "surfactant" refers to an organic compound that contains both a hydrophobic group and a hydrophilic group. The hydrophilic group is often referred to as the head and the hydrophobic group as the tail. A surfactant will adsorb at interfaces between hydrophilic compositions, such as oil, and hydrophilic compositions, such as water, wherein the hydrophilic head will extend into the water and the hydrophobic tail will extend into the oil. As used herein, a "anionic surfactant" is a surfactant that contains an anionic functional group or groups at its hydrophilic head. Non-limiting examples of an anionic function groups are sulfate, sulfonate, phosphate, and carboxylates. As used herein, a "nonionic surfactant" are surfactants that do not contain a charged functional group. Non-limiting examples of non-ionic surfactants are fatty alcohols.

C. Terms Related to Methods of Treatment

As used herein, "oral administration" refers to treatment of a disease or disorder by delivery of therapeutically effective agents through the mouth. The agent may permeate through the oral mucosa or anywhere throughout the gastrointestinal tract. Oral administration includes, but is not limited to, solid dosage forms such as tablet, chewable tablet, lozenge, powder, dissolving film, gum, as well as homogenous and heterogeneous liquids, including emulsions.

"Inraoral route of delivery" is a route of administering that applies to products intended to deliver the drug substance within the mouth, e.g. Buccal, Lingual, or Periodontal. [Guidance for Industry and Review Staff. Nonclinical Safety Evaluation of Reformulated Drug Products and Products Intended for Administration by an Alternate Route. FDA 2008, p. 6 line 243].

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection.

A "subject" or a "patient" refers to any mammal (e.g., a human), such as a mammal that may be susceptible to a disease or disorder, for example, diabetes. Examples include a human, a non-human primate, a cow, a horse, a pig, a sheep, a goat, a dog, a cat, or a rodent such as a mouse, a rat, a hamster, or a guinea pig. In various embodiments, a subject refers to one that has been or will be the object of treatment, observation, or experiment. For example, a subject can be a subject diagnosed with diabetes or otherwise known to have diabetes or is a subject selected for treatment, observation, or experiment on the basis of a known diabetes in the subject.

As used herein, "treat," "treatment" or "treating" refers to an amelioration of a disease or disorder, or at least one sign or symptom thereof. In another embodiment, "treatment" or "treating" refers to an amelioration of at least one measurable physical parameter, not necessarily discernible by the patient. In yet another embodiment, "treatment" or "treating" refers to reducing the progression of a disease or disorder, for example, by reducing the rate of disease progression compared to a reference population having the same disease or decreasing the degree or rate or progression of a sign or symptom in the subject prior to treatment. In yet another embodiment, "treatment" or "treating" refers to delaying the onset of a disease or disorder, e.g., compared to a reference population or other method of determining such a parameter as is known by those in the art.

The phrase "therapeutically effective amount" as used herein means that amount of therapeutic effective agent that is effective for producing a desired therapeutic effect. Accordingly, a therapeutically effective amount treats or prevents a disease or a disorder, ameliorates at least one sign or symptom of the disorder, e.g., lowers a diabetic patient's glucose level. In various embodiments, the disease or disorder is a diabetes.

The term "therapeutic effect" is art-recognized and refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and conditions in an animal or human.

The terms "systemic administration," "administered systemically," "peripheral administration" and "administered peripherally" are art-recognized and refer to the administration of a composition, therapeutic or other material other than directly into the central nervous system, such that it enters the patient's system and, thus, is subject to metabolism and other like processes, for example, intravenous, subcutaneous, or oral administration.

D. Terms Related to Pharmaceutics

The term "pharmaceutically acceptable counter ion" refers to a pharmaceutically acceptable anion or cation. In various embodiments, the invention comprises a pharmaceutically acceptable counter ion. The pharmaceutically acceptable counter ion is a pharmaceutically acceptable ion. Non-limiting examples include, but are not limited to citrate, matate, acetate, oxalate, chloride, bromide, iodide, nitrate, sulfate, bisulfate, phosphate, acid phosphate, isonicotinate, acetate, lactate, salicylate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)).

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Therapeutically effective agents included in the present compositions that include an amino moiety may form pharmaceutically acceptable salts with various amino acids, in addition to the acids mentioned above. Therapeutically effective agents included in the present compositions, that are acidic in nature are capable of forming base salts with various pharmacologically acceptable cations. Examples of such salts include alkali metal or alkaline earth metal salts and ammonium salts.

In addition, if the therapeutically effective agents described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

A pharmaceutically acceptable salt can be derived from an acid selected from 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, hydrochloric acid, isethionic, isobutyric acid, lactic acid, lactobionic acid, lauric acid, maleic acid, malic acid, malonic acid, mandelic acid, methanesulfonic acid, mucic, naphthalene-1,5-disulfonic acid, naphthalene-2-sulfonic acid, nicotinic acid, nitric acid, oleic acid, oxalic acid, palmitic acid, pamoic acid, pantothenic, phosphoric acid, proprionic acid, pyroglutamic acid, salicylic acid, sebacic acid, stearic acid, succinic acid, sulfuric acid, tartaric acid, thiocyanic acid, toluenesulfonic acid, trifluoroacetic, and undecylenic acid.

The term "bioavailable" is art-recognized and refers to a form of the subject disclosure that allows for it, or a portion of the amount administered, to be absorbed by, incorporated to, or otherwise physiologically available to a subject or patient to whom it is administered.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the formulation and not injurious to the patient.

II. FORMULATION COMPOSITION

The present teachings provide intraoral solid pharmaceutical compositions for sublingual or buccal administration, containing a biologically active peptide, such as insulin or insulin analogs, glucagon-like peptide and analogs (e.g., GLP-1, exenatide, liraglutide), calcitonin, oxytocin, vasopressin, octreotide, leuprolide, gosereline, enkephalins, endorphins, interferons, interleukins, integrilin, parathyroid hormone agonists and antagonists (e.g., Tiraparatide, Eptifibatide), natriuretic hormone (Nesiritide), growth factors, necrosis factors, etc. The object of the invention is to provide safe and convenient method for transmucosal delivery of biologically active peptide, providing fast onset of biological action.

In various embodiments, the disclosure permeates therapeutically active agent through the oral mucosa. In various embodiments, the invention permeates a therapeutically active agent through the buccal mucosa. In a various embodiments, the formulation permeates a therapeutically active agent through the sub-lingual mucosa. The invention may permeate 1, 2, 3, or 4 therapeutically active agents through the oral, buccal or sub-lingual mucosa.

In one embodiment, the solid, semi-solid or liquid self-emulsifying composition for intraoral transmucosal delivery of biologically active peptides and proteins (a) spontaneously forms emulsion upon contact with a body fluid or water containing medium, (b) the composition comprises an oil phase, a surfactant or mixture of surfactants and a physiologically acceptable hydrophobic counter-ion; (c) said counter-ion forms a salt or a non-covalent complex with peptide or protein; (d) the formed peptide complex completely dissolved in the composition; (e) the oil phase of the emulsion contains at least one physiologically acceptable aromatic solubilizing compound which provides complete solubilization of the peptide complex; (f) upon forming of the emulsion, complex of the counter-ion and biologically active peptide remains entirely associated with the oil droplets of the formed emulsion; (g) biologically active peptide or protein remains completely dissolved in the oil phase of the formed emulsion.

A. Therapeutically Active Agents

The present teachings are useful for a variety of therapeutic agents that are known and may be identified by their effects. In some embodiments, the active agent is selected from a biomolecule, bioactive agent, small molecule, drug, prodrug, drug derivative, protein, peptide, vaccine, adjuvant, imaging agent (e.g., a fluorescent moiety) or polynucleotide. In various embodiments therapeutically active agents form pharmaceutically acceptable salts. In various embodiments therapeutically active agents form complexes with pharmaceutically acceptable counter-ions.

In various embodiments the therapeutically active agent is a peptide. Non-limiting examples of therapeutically active peptides include calcitonins, vasopressins, leuprolide, octreotide, glucagon-like peptides, liraglutide, pramlintide, glatiramer, oxytocin, somatostatin, icatibant, hirudin, corticorelin, angiotensin antagonists, cholecystokinin analogues, ziconotide, bradykinin inhibitors, other peptides derivatives and analogues.

In various embodiments the therapeutically active agent is a protein or protein derivative. In other embodiments, the biologically active peptide or protein is selected from group of insulins, insulin analogs, insulin growth factor, proinsulin, C-peptide, amylin, pramlintide, glucagon-like peptide (GLP), GLP-1 analogs, liraglutide, rusalatide, semaglutide, calcitonin, somatostatin, vasopressin, oxytocin, GNRH antagonists, octreotide, leuprorelin, goserelin, triprorelin, enkephalins, endorphins, interferons, interleukins, parathyroid hormone agonists, teriparatide, integrilins, natriuretic hormone, tumor necrosis factors growth factors, and necrosis factors.

Peptides and Proteins
i. Insulin

Two-chain polypeptide hormone produced by the beta cells of pancreatic islets. The molecular weight of monomeric insulin is ~5807 Da. Insulin regulates the cellular uptake, utilization, and storage of glucose and inhibits the breakdown of glycogen, proteins and fats. Bovine, swine and human recombinant insulins as well as different insulin analogs are used in treatment of diabetes mellitus.

ii. Insulin Analogs

Insulin glulisine (Apidra™) and insulin lispro (HUMALOG®) are rapid-acting human insulin analog used to lower blood glucose. Structurally glulisine is 3B-lysine29B-glutamic acid-human insulin, molecular weight ~5823 Da, and lispro differs from human insulin in proline at B28 is replaced by lysine and the lysine in B29 is replaced by proline. Chemically lispro is Lys(B28), Pro(B29) human insulin analog with molecular weight of 5808 Da.

iii. Vasopressin [$Arg^8$ or $Lys^8$]

Nonapeptide Cys-Tyr-Phe-Gln-Asn-Cys-Pro-Arg/Lys-Gly-NH2 [Disulfide Bridge: 1-6]

Molecular weight, Dalton: 1084 (Arg)/1056 (Lys)

Endogenous antidiuretic hormone in most mammalian species. $Arg^8$-vasopressin is also a neurotransmitter in the central nervous system. It is implicated in a variety of physiological processes including diuresis, vasoregulation and memory; regulates water balance by antidiuretic action; contracts arterioles (vasopressor action). $Lys^8$-Vasopressin is a predominant form of vasopressin present in pigs and marsupials.

iv. Calcitonin 32-amino acids polypeptide, MW ~3432 Da. (salmon calcitonin)

Hypocalcemic hormone. Decreases blood calcium and phosphate due to inhibition of resorption by osteoblasts and osteocytes.

v. Exenatide

Exenatide is a 39-amino-acid peptide (Molecular weight ~4,187 Da), an insulin secretagogue, with glucoregulatory effects. It is a synthetic version of exendin-4, a hormone similar to human glucagon-like peptide-1 (GLP-1) which regulates glucose metabolism and insulin secretion. Exenatide enhances glucose-dependent insulin secretion by the pancreatic beta-cell, suppresses inappropriately elevated glucagon secretion, and slows gastric emptying, although the mechanism of action is still under study.

Glucose regulation action is also demonstrated by amylin (MW 3906.3) and pramlintide (MW 3951.4).

vi. Liraglutide

Liraglutide, Lys(γ-Glu-palmitoyl)26,Arg34)-GLP-1(7-37), Molecular weight 3,751 Da., is a long-acting glucagon-like peptide-1 (GLP-1) analog. As GLP-1, liraglutide induces insulin secretion from β-cells by binding to GLP receptors in the pancreas. Liraglutide injections used for improvement of glycemic control in adults with type 2 diabetes mellitus.

vii. Rusalatide

Rusalatide (Crysalin) is a 23 amino acid peptide (Ala-Gly-Tyr-Lys-Pro-Asp-Glu-Gly-Lys-Arg-Gly-Asp-Ala-Cys-Glu-Gly-Asp-Ser-Gly-Gly-Pro-Phe; MW 2311.5 as acetate), structurally related to thrombin and showing multiple biological activities.

viii. Natriuretic Hormone

Natriuretic hormone, B-type natriuretic peptide (nesiritide, NATRECOR®): a 32-amino-acid polypeptide with molecular weight 3464 Da., secreted by the ventricles of the heart in response to excessive stretching of heart muscle cells. Nesiritide relaxes and dilates blood vessels, lowering blood pressure, and improves breathing in people with congestive heart failure (CHF).

ix. Triptorelin; Leuprorelin, and Goserelin

Triptorelin (decapeptide pGlu-His-Trp-Ser-Tyr-D-Trp-Leu-Arg-Pro-Gly-NH2, pGlu=L-Pyroglutamyl, MW=1311.5 Da.; leuprorelin (nonapeptide pGlu-His-Trp-Ser-Tyr-D-Leu-Leu-Arg-Pro-NHEt, MW 1209 Da.) and goserelin (decapeptide Pyr-His-Trp-Ser-Tyr-D-Ser(TBu)-Leu-Arg-Pro-azaGly-NH2, MW 1269.4 Da.) are synthetic gonadotrophin releasing hormone (GnRH), analogues, also known as luteinizing hormone-releasing hormone (LHRH) receptor agonists that approved for treatment of a number of indications including prostate cancer, endometriosis and uterine fibroids.

x. Parathyroid Hormone (PTH) Agonists

Parathyroid hormone (PTH) agonists, e.g., Teriparatide (human PTH hormone, FORTEO®)-34-amino acids polypeptide (Ser-Val-Ser-Glu-Ile-Gln-Leu-Met-Hi s-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe-OH, MW 4117.7 Da.), intended for osteoporosis treatment.

xi. Somatostatin

Somatostatin, also known as growth hormone-inhibiting hormone (GHIH) or somatotropin release-inhibiting factor (SRIF) is a peptide hormone that regulates the endocrine system and affects neurotransmission and cell proliferation via interaction with G protein-coupled somatostatin receptors and inhibition of the release of numerous secondary hormones. Somatostatin inhibits insulin and glucagon secretion. One od Somatostatin forms contains 14 amino acids and has molecular weight 1638 Da.

xii. Sandostatin

Sandostatin (octreotide)—synthetic octapeptide, MW ~1019 Da. Intended for treatment of acromegaly.

xiii. Oxytocin

Oxytocin—nonapeptide (molecular weight ~1007 Da.), manufactured in hypothalamus. An intravenous infusion of oxytocin is used to induce labor and to support labor in case of slow childbirth.

B. Counter Ions

Non-limiting examples of counter ions are diacylphosphatidylglycerol derivatives such as dimyristoyl-, dioleyl-, dipalmitoyl- and distearoyl phosphatidylglycerols, -tocopheryl succinate, tocopheryl phosphate, sodium dioctylsulfosuccinate, mono- and disubstituted cetylphosphates, cholates, deoxycholates, ammonium glycyrrhizinate, cholesteryl hemisuccinate, cholesteryl sulfate, and cholesteryl sulfate.

In one embodiment, the counter ion has a molecular weight not less than about 100 Dalton, not less than about 200 Dalton, not less than about 300 Dalton, not less than about 400 Dalton, not less than about 500 Dalton, not less than about 600 Dalton. More preferably, the counter ion has a molecular weight not less than about 100 Dalton, not less than about 600 Dalton.

C. Aromatic Solubilizing Compound

In one embodiment, the composition comprises at least one aromatic compound. The aromatic compound is selected from the group comprising synthetic or natural esters of salicylic acid, cinnamyl esters, phenyl, phenethyl and benzyl esters and ethers, aromatic flavoring compounds, phenethyl acetate, anisole, or mixture thereof.

In another embodiment, the aromatic compound is selected from group of wintergreen oil, methyl salicylate, ethyl salicylate, octyl salicylate, benzyl salicylate, amyl salicylate, isoamyl salicylate, butyl salicylate, isobutyl salicylate, phenyl salicylate, tolyl salicylate, ethylhexyl salicylate.

In yet another embodiment, the aromatic compound is methyl salicylate.

In one embodiment, the methyl salicylate is present in an amount from about 0.1% to about 90%, from about 10% to about 80%, from about 20% to about 70%, from about 30% to about 60%, from about 40% to about 50%, or about 50% by weight of the composition. In yet another embodiment, the methyl salicylate is present in an amount from about 0.1% to about 50% by weight of the composition.

D. Formation of the Oil-in-Water Emulsion

In another aspect of the invention, therapeutically active agent and counter-ion incorporated into a self-emulsifying composition, forming oil-in-water emulsion.

In one embodiment, the molar ration of the therapeutically active agent: counter-ion is about 1:10, about 1:9, about 1:8, about 1:7, about 1:6, about 1:5, about 1:4, about 1:3, about 1:2, about 1:1, about 10:1, about 9:1, about 8:1, about 7:1, about 6:1, about 5:1, about 4:1, about 3:1, about 2:1.

In various embodiments, the droplet size of the formed oil-in-water emulsion is less than 1 μm, less than 2 μm, less than 3 μm, less than 4 μm, less than 5 μm, less than 10 μm, less than 15 μm, or less than 20 μm. In other embodiments, the droplet size is between about 5 nm and about 1000 nm, between about 2 nm and about 200 nm, between about 10 nm and 300 nm, between about 15 nm and 100 nm, or between about 20 nm and about 60 nm.

In one embodiment, the solubility of the therapeutically active agent is less than about 0.1 mg/ml, less than about 0.2 mg/ml, less than about 0.5 mg/ml, less than about 2 mg/ml, less than about 5 mg/ml, less than about 6 mg/ml, less than about 10 mg/ml, less than about 20 mg/ml, or less than about 30 mg/ml. In another embodiment, the solubility of the therapeutically active agent is about 1 mg/ml, about 2 mg/ml, about 3 mg/ml, about 4 mg/ml, about 5 mg/ml, about 10 mg/ml, about 15 mg/ml, about 20 mg/ml, about 25 mg/ml, about 30 mg/ml, about 35 mg/ml, or about 40 mg/ml. In yet another embodiment, the solubility of the therapeutically active agent is greater than about 40 mg/ml.

In another embodiment, the oil phase may additionally comprise phospholipids, glycerides, fatty acid esters, vitamin E, vitamin E esters, natural and synthetic terpenes or essential oils.

In one embodiment, the composition additionally comprises at least one physiologically acceptable chelating agent, preventing precipitation of the counter-ion in presence of divalent metal ions in body fluids. In yet another embodiment, the chelating agent is selected from the group comprising EDTA, EGTA, bile acids, citric acid, lactic acid, amino acids and physiologically acceptable salts thereof.

In another embodiment, the chelating agent in present in an amount from about 0.1 mg to about 10 mg, from about 1 mg to about 5 mg of the chelating agent per dose to bind calcium or magnesium upon contact of the dosage form with body fluid.

In one embodiment, the molecular ratio between the counter-ion molecule and the basic amino acid residue in the peptide is in the range from 1: (N+1) to about (N+1):(N+1) per chain for non-cyclic peptides; for cyclic peptides the ratio is from about 1:N to about N:N, where N is a number of basic amino acids in the peptide chain.

III. EXAMPLES

The following examples illustrate the features and scope of the present invention. These examples should not be considered as any limitations, but should be merely interpreted to teach how to make the efficient colloidal drug delivery systems.

Insulin is a polypeptide with molecular weight of the monomer unit about 6000 Dalton. Due to simple method of biological activity testing by decrease of blood glucose, insulin can be used as a convenient compound for confirmation of transmucosal delivery of the peptide.

Example 1: Solubilization of Insulin in Different Oil Phases

Initial oil phase, containing capric/caprylic triglycerides (medium chain triglycerides, MCT oil), tocopherol acetate, lecithin and 1-Menthol, was prepared by dissolving all components in ethyl alcohol followed by solvent removal. The obtained oil phase was used "as is" or after mixing with ester of salicylic acid (10, 25 and 40% w/w).

Pure crystalline insulin (bovine or human recombinant) was mixed with excess of the counter-ion (molar ratio peptide:counter-ion at least 1:5, i.e., not less than 5 mol of the counter-ion per 1 mol of the peptide), added to the oil phase and slightly heated for 10-20 minutes. Solubility was estimated visually. Some of obtained results presented in table 1.

TABLE 1

Insulin solubility in oil phases in presence and absence of Methyl Salicylate

| Counter-ion | MCT oil only | Methyl Salicylate concentration in MCT-Vit.E-Menthol-Lecithin oil phase | | | | Comment |
| --- | --- | --- | --- | --- | --- | --- |
| | | 0% | 10% | 20% | 40% | |
| | Insulin solubility in the oil phase at room temperature | | | | | |
| Tocopheryl phosphate | <0.1 mg/ml | <0.2 mg/ml | <0.5 mg/ml | ~2 mg/ml | ~5 mg/ml | |
| Tocopheryl succinate | <0.1 mg/ml | ~0.2 mg/ml | ~0.5 mg/ml | ~2.5 mg/ml | ~6 mg/ml | |
| Cholesteryl sulfate | <0.1 mg/ml | <0.1 mg/ml | ~0.5 mg/ml | ~2 mg/ml | ~6 mg/ml | |
| Desoxycholic acid | ~0.1 mg/ml | <0.5 mg/ml | ~2 mg/ml | ~5 mg/ml | ~8 mg/ml | |
| Dicetylphosphate | ~0.1 mg/ml | <1 mg/ml | ~3 mg/ml | ~10 mg/ml | ~15 mg/ml | Gelling, m.p.~32° C. |
| Dimyristylphosphatidylglycerol | <0.1 mg/ml | ~1 mg/ml | ~10 mg/ml | ~30 mg/ml | >40 mg/ml | |
| Distearoylphosphatidylglycerol | ~0.1 mg/ml | ~1 mg/ml | ~8 mg/ml | ~20 mg/ml | >30 mg/ml | Gelling, m.p.~35° C. |

Insulin contains two peptide chains with four basic aminoacids in B-chain (Lys, Arg and two His) and two $NH_2$-end aminoacids (Gly in A-chain and Phe in B-chain). Experiments showed that for example, at molar ratio of DMPG or DSPG to insulin less than 4:1 hydrophobization of insulin is not complete and only part of the peptide is associated with the oil phase while at molar ratios 5:1, 6:1, 8:1 and higher practically all insulin remains incorporated into the oil phase. Increase of the molecular mass of used counter-ion improves hydrophobization, as was demonstrated by octanol-water partition experiments.

Solid dosage forms (tablets) contained insulin were prepared by wet granulation, followed by drying of the granulation, comminuting, screening, mixing with bulking agent (filler), glidant and lubricant. Sweetener, flavor, disintegrant also can be added to a granulation. Tablets (round or oval shape) were compressed using single punch tablet press and appropriate tooling.

TABLE 2

| Example # | 1 | 2 | 3 | 4 | 5 | 6 | 7 | 8 | 9 |
|---|---|---|---|---|---|---|---|---|---|
| Insulin | 2.2 | 2 | 2 | 2.2 | 2.2 | 2.2 | 2.2 | 2.2 | 2 |
| Lecithin | 5 | 10 | 7.5 | 7.5 | 7.5 | 10 | 7.5 | 10 | 10 |
| PEG-40 stearate | 20 | 20 | 10 | | | | | | 10 |
| PEG-40 castor oil (hydrogenated) | | | | 10 | 8 | 8 | 8 | 8 | 6 |
| Polyvinylpyrrolidone K-90 | 15 | 15 | | | | | | | |
| Polyvinylpyrrolidone (PVP K-25) | | | 5 | 10 | 10 | 10 | 10 | 10 | 5 |
| Crospovidone | | | 10 | | | | | | 10 |
| Menthol | | 1.2 | 1.8 | 4.8 | 5 | 2 | | 5 | 2 |
| Peppermint oil | | | 5 | 3 | 3 | | | | 5 |
| Wintergreen oil | | | | | | | 10 | | |
| MCT | 6 | 6 | | | | 4 | 4 | 5 | 4 |
| dl-alpha Tocopherol acetate | | | | 2 | 2 | 4 | 2 | | |
| Methyl salicylate | | | | | 5 | 10 | | | |
| Ethyl salicylate | | | | | | | 6 | | |
| Benzyl salicylate | | | | | | | | 8 | |
| Anisole | | | | | | | | | 8 |
| d-alpha Tocopheryl acid succinate | 0.3 | 0.3 | 0.75 | 1.2 | 1.2 | 1.2 | 1.2 | 1 | 0.8 |
| Desoxycholate Na | | | 8 | | 5 | | 5 | | 10 |
| Dioctylsulfosuccinate | 3 | | | | | 10 | | | |
| Dicetyl phosphate | | | | | | | | 2 | |
| Cholesteryl sulfate K | | | | 5 | | | | | |
| DMPG | | 7.5 | 10 | | | 3 | 3 | | |
| DSPG | | | | | | | | 2 | |
| Glycyrrhizinate NH$_4$ | | 10 | | 10 | | | | | 10 |
| Oleic acid | | | | | | | | | 1 |
| Lactic acid | | | | | | | | 1 | |
| Acetic acid | | | | 2 | 2 | | | 1 | 1 |
| Sucralose | 1 | | 1 | | 1 | 1 | 1 | 1 | |
| Silicon dioxide | 15 | 16 | 15 | 14 | 15 | 12 | 18 | 12 | 15 |
| PEG 3350 | 5 | 5 | 5 | 5 | 5 | 5 | 5 | 5 | 5 |
| Mannitol | 200 | | | 180 | 120 | 120 | 120 | 120 | 140 |
| Sorbitol | | 220 | 140 | 100 | 150 | 150 | 150 | 200 | 140 |
| Tablet weight, mg | 272.5 | 313 | 221.05 | 356.7 | 344.9 | 352.4 | 351.9 | 391.2 | 384.8 |

TABLE 3

| Example # | 10 | 11 | 12 | 13 | 14 | 15 | 16 | 17 | 18 |
|---|---|---|---|---|---|---|---|---|---|
| Insulin (human recombinant) | 2 | 2 | 2 | 2 | 1.1 | 2 | | 1.1 | 1.1 |
| Insulin glulysine (Apidra) | | | | | | | 1.1 | | |
| Lecithin | 10 | 5 | 7.5 | 15 | 10 | 7.5 | 10 | 10 | 5 |
| PEG-40 stearate | 30 | 10 | 10 | 6.5 | | | | | |
| PEG 40 castor oil (hydrogenated) | | | | 3.5 | 6.5 | 8 | 8 | 6.5 | 6 |
| TPGS | | | | | 5.5 | | 8 | 5.5 | |
| Choleth-24 | | | | | | 6 | | | 10 |
| Polyvinylpyrrolidone (PVP K-25) | 5 | 5 | | 5 | 8 | 5 | 5 | 9 | |
| Crospovidone | | 10 | | | | | 10 | | |
| Menthol | 1.8 | 1.8 | 5 | 5 | 3 | 5 | 5 | 3 | 4 |
| MCT | 2 | 5 | | 12 | 3 | | 4 | 3 | 5 |
| dl-alpha Tocopherol acetate | 5 | 5 | 2 | 4 | 1.8 | 4 | 4 | 1.8 | 3 |
| Methyl salicylate | | | | | 4 | | 6 | | |
| Ethyl salicylate | | | | | | | | 6 | |
| Benzyl salicylate | | | | | | 5 | | | 8 |
| Wintergreen oil | | | | | | | | 9 | |
| d-alpha Tocopherol acid succinate | 1.2 | 1 | 1.2 | 1.2 | 0.6 | 1.5 | 1.2 | 0.6 | 0.8 |
| Sodium deoxycholate | 10 | 8 | | | | 8 | | | |
| Dioctylsulfosuccinate | | | | | | | | | 4 |
| Cholesteryl sulfate | | | | | | | | | |
| DMPG | 10 | | 2 | 4 | 0.8 | 10 | 1 | 0.8 | |
| DSPG | | 2 | | | | | | | |
| EDTA disodium dihydrate | | 1 | | | 2 | 4 | 2 | 2 | 2 |

TABLE 3-continued

| Example # | 10 | 11 | 12 | 13 | 14 | 15 | 16 | 17 | 18 |
|---|---|---|---|---|---|---|---|---|---|
| Glycerol | 8 | | | 2 | 1 | 2 | 2 | 1 | 1 |
| Succinic acid | 12 | | | | | | | | 2 |
| Acetic acid | | | 1.2 | 1.2 | 2 | 1.8 | 1.8 | 1.8 | 1.8 |
| Sucralose | 1.5 | 1 | 1 | 1 | | 1 | | | |
| Silicon dioxide | 20 | 15 | 22 | 32 | 2 | 15 | 18 | 2 | 8 |
| PEG 3350 | 6 | 5 | 5 | 5 | 5 | 5 | 5 | 5 | 5 |
| Maltodextrin | | | | | 120 | | | 120 | 140 |
| Mannitol | 80 | 60 | 150 | 150 | 30 | 60 | 60 | 35 | 80 |
| Sorbitol | 180 | 140 | 50 | 100 | 210 | 180 | 220 | 205 | 100 |
| Tablet weight, mg | 384.5 | 276.8 | 258.9 | 349.4 | 415.5 | 330.8 | 372.1 | 432.6 | 386.7 |

TABLE 4

| Example # | 19 | 20 | 21 | 22 | 23 | 24 | 25 | 26 | 27 |
|---|---|---|---|---|---|---|---|---|---|
| Insulin | 1.1 | 1.1 | 1.1 | 1.1 | 1.1 | 1.1 | | 1.1 | 1.1 |
| Insulin analog (Glulysine) | | | | | | | 1.1 | | |
| Lecithin | 10 | 10 | 10 | 10 | 10 | 5 | 5 | 5 | 5 |
| PEG-40 stearate | | | | | 8 | 8 | | | |
| PEG 40 castor oil (hydrogenated) | 7.5 | 8 | 10 | | | | 6 | 6 | 10 |
| TPGS | | | | | | | 8 | | |
| Choleth-24 | | | | | 10 | | | 8 | |
| Tyloxapol | | | | 10 | | 6 | | | 8 |
| Polyvinylpyrrolidone (PVP K-25) | 8 | 8 | 8 | 8 | 8 | 10 | | | 8 |
| Crospovidone | | 10 | | | | 8 | | | |
| Menthol | 4 | 5 | 4 | 5 | 5 | 3 | 3 | 3 | 4 |
| Peppermint oil | 4 | | | | | 4 | | 4 | |
| Wintergreen oil | | | | 9 | | | | | |
| MCT | 4 | | | 4 | 5 | 5 | | | |
| Acetylated monoglycerides | | 4 | | | | | 5 | 5 | 5 |
| dl-alpha Tocopherol acetate | 2 | 5 | 4 | 4 | 4 | 4 | 4 | | 2 |
| Methyl salicylate | | 8 | 10 | | 8 | 9 | 9 | | |
| Ethyl salicylate | 8 | | | | | | | | |
| Anisole | | | | | | | | 10 | |
| Eugenol | | | | | | | | | 10 |
| d-alpha Tocopherol acid succinate | | 1.2 | 1 | 1.2 | 1.2 | 0.8 | 0.8 | 0.8 | 1 |
| d-alpha Tocopherol | 2 | | | | 1 | 1 | 1 | 1 | 1 |
| Cholesteryl sulfate | 1 | | | | | | | | |
| DMPG | | 1.2 | 1.2 | | | | | | 0.8 |
| DSPG | | | | | 1 | 1 | 0.9 | 0.9 | |
| Glycyrrhiz. Ammonium | | | | | 10 | | | | |
| Lactic acid | | | | 1 | | | | 1 | 1 |
| Citric acid | | | | | 2 | 2 | 2 | | |
| Acetic acid | 1.8 | 1.8 | 1.5 | 1.5 | 1.8 | 1.8 | 1.8 | 1.5 | 1.5 |
| Starch (pregelatinized) | | | | | | | 10 | 10 | |
| Silicon dioxide | 20 | 20 | 20 | 18 | 4 | 16 | 5 | 22 | 24 |
| PEG 3350 | 5 | 5 | 5 | 5 | 5 | 5 | 5 | 5 | 5 |
| Maltodextrin | | | | | | 120 | 120 | | |
| Mannitol | 80 | 60 | 50 | 60 | 80 | 40 | 60 | 80 | 80 |
| Sorbitol | 220 | 240 | 220 | 220 | 200 | 120 | 120 | 200 | 200 |
| Tablet weight, mg | 378.4 | 388.3 | 345.8 | 357.8 | 357.1 | 370.7 | 377.6 | 368.3 | 357.4 |

Glucose lowering activity (calculated by AUC 0-180 min ratios for drug and placebo): Freshly prepared (Stored 1 day) - 36.8% Day 92 6.9%

Example 2: Liquid Composition

Liquid formulation was prepared using same components but instead of incorporation into a tablet pure insulin was dissolved in the oil and surfactant mixture with help of acids and counter-ion and then a physiologically acceptable organic solvent was added. Antioxidant, sweeteners, flavors, chelating agents can be also added to a liquid formulation.

Figure 1:
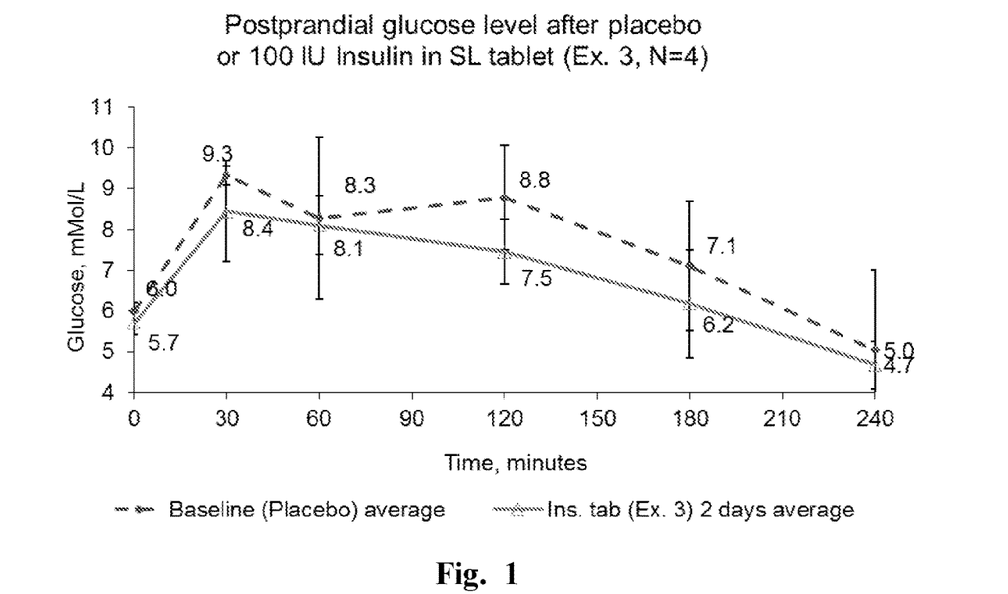
FIG. 1: Postprandial glucose levels in healthy volunteers after placebo or sublingual insulin (100 IU) for freshly prepared tablet formulation (Ex. 3).

Freshly prepared tablets with insulin in self-emulsifying compositions shows pronounced hypoglycemic action after sublingual administration, as presented at FIG. 1.

Figure 2:
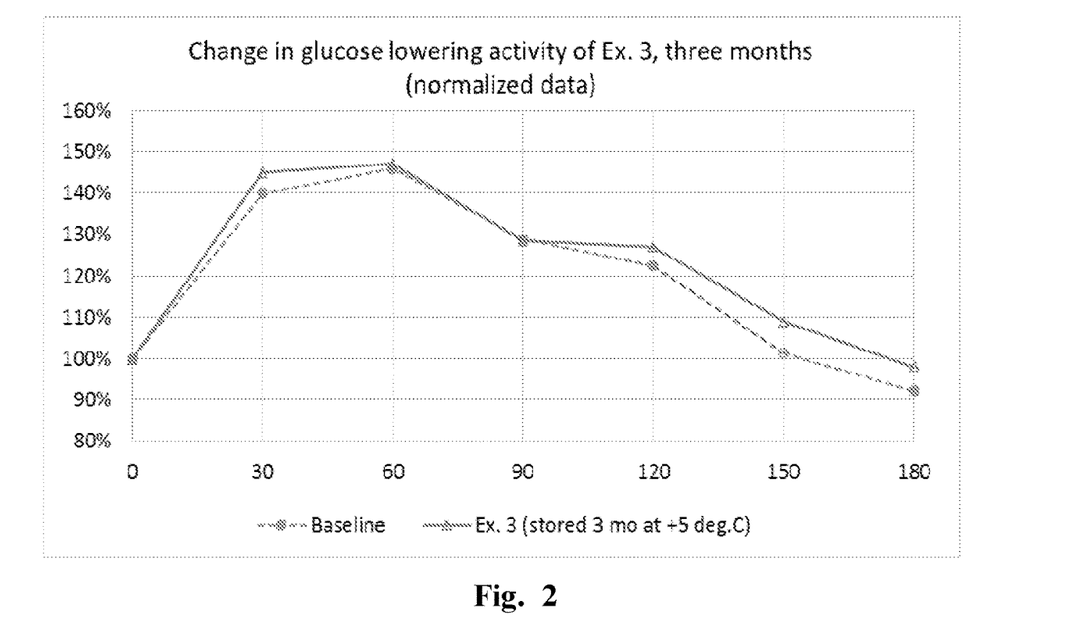
FIG. 2: Postprandial glucose levels in healthy volunteers after placebo or sublingual insulin (100 IU) for the same formulation stored 3 months.

However, after 3 months of storage glucose lowering action drastically decreases (FIG. 2).

Figure 3:
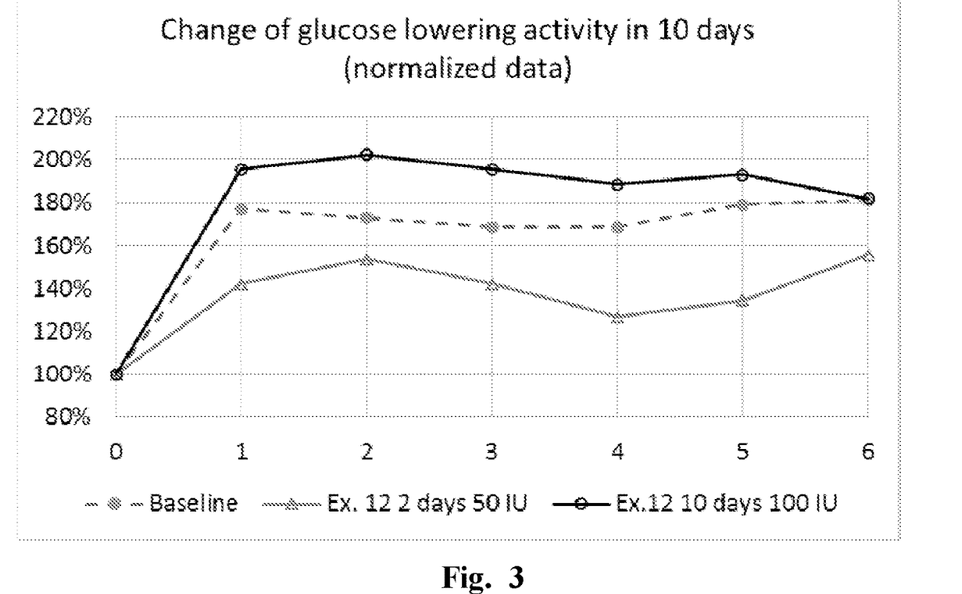
FIG. 3: Postprandial glucose levels in healthy volunteers after placebo or sublingual insulin (50 IU) for freshly prepared tablet formulation (Ex. 12) and for the same formulation stored 10 days.
Figure 4:
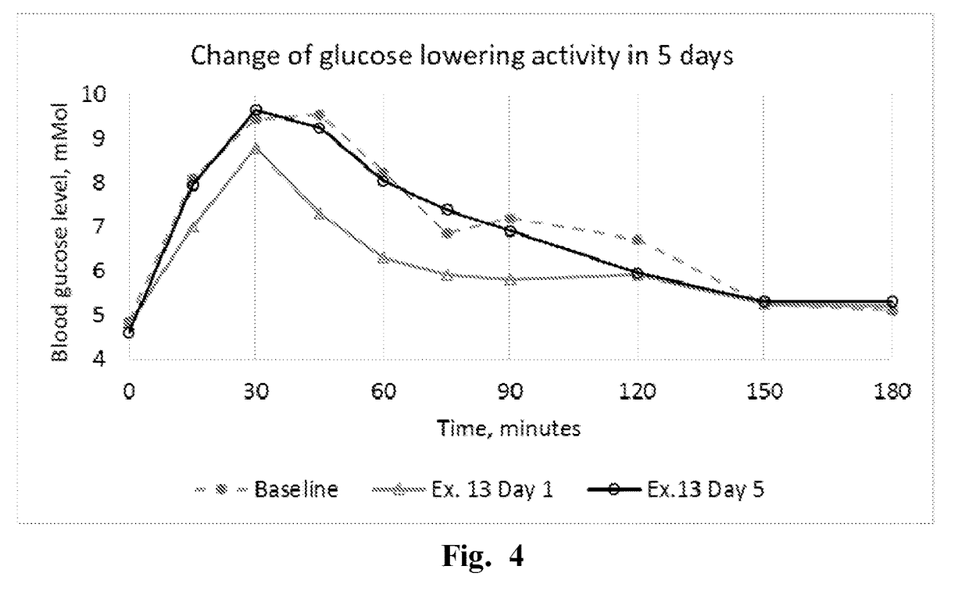
FIG. 4: Postprandial glucose levels in healthy volunteers after placebo or sublingual insulin (25 IU) for freshly prepared tablet formulation (Ex. 13) and for the same formulation stored 5 days.

Such drop in pharmacological outcome was observed for tablets, stored for 10 and even 5 days (FIG. 3, 4). It was determined that loss of biological activity associated with 
decrease of the peptide complex solubility in the oil phase, followed by crystallization and precipitation of the complex.

Figure 5:
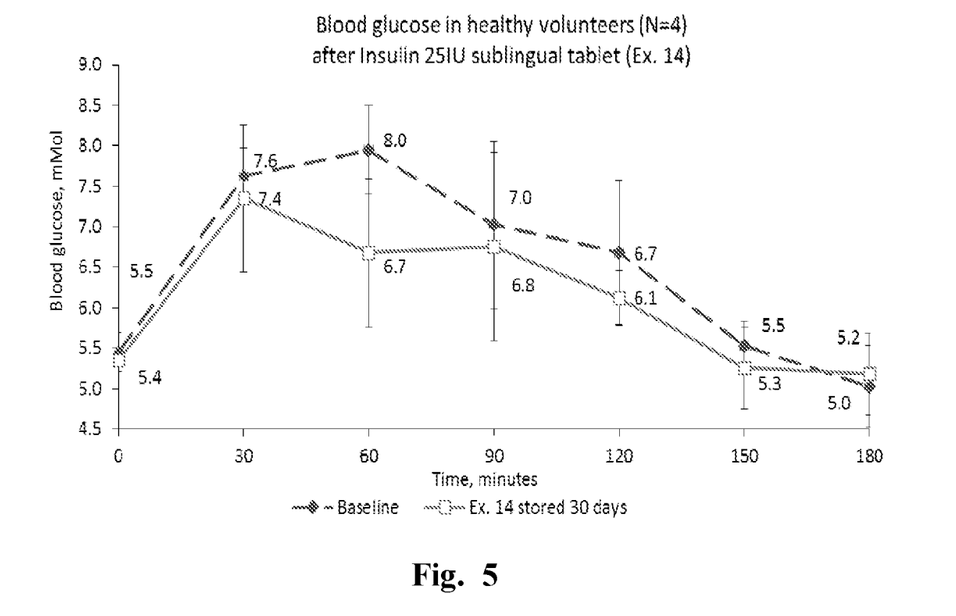
FIG. 5: Postprandial glucose levels in healthy volunteers after placebo or sublingual insulin (25 IU) for tablet formulation containing salicylate ester (Ex. 14) after 30 days storage.
Figure 6:
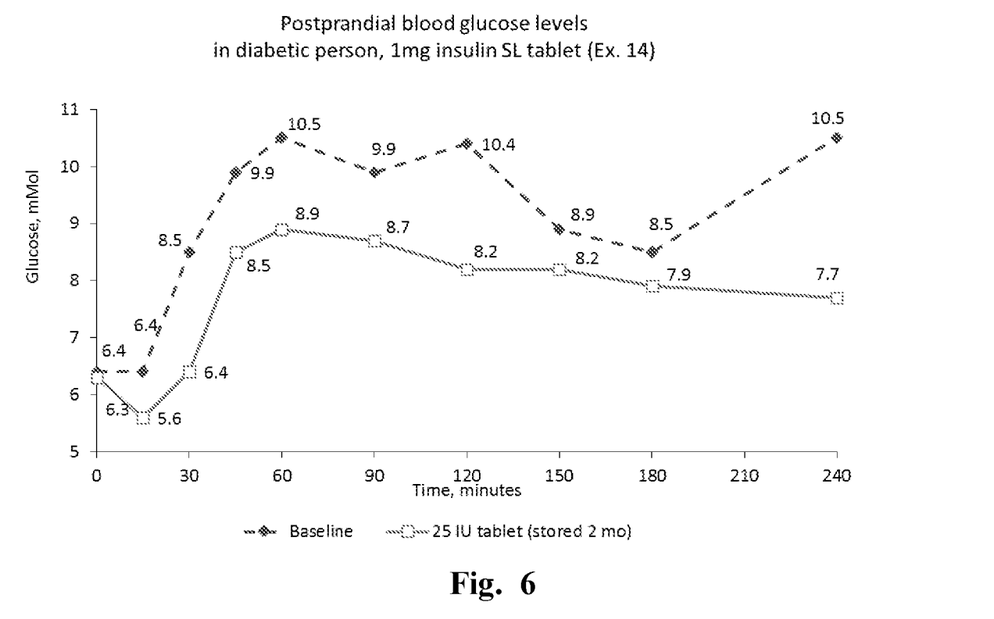
FIG. 6: Postprandial glucose levels in diabetic person after placebo or sublingual insulin (25 IU) for tablet formulation containing salicylate ester (Ex. 14) stored 2 months.

Incorporation of aromatic compounds such as salicylate esters, wintergreen oil or similar significantly increases solubility of the peptide-counter ion complex (Table 1) and prevents loss of biological activity during extended period of storage either at ambient conditions or in refrigerator (FIG. 5, 6). All selected salicylic esters and other aromatic compounds are presented in FCC and may be safely used as flavor components in food or medicines.

Figure 7:
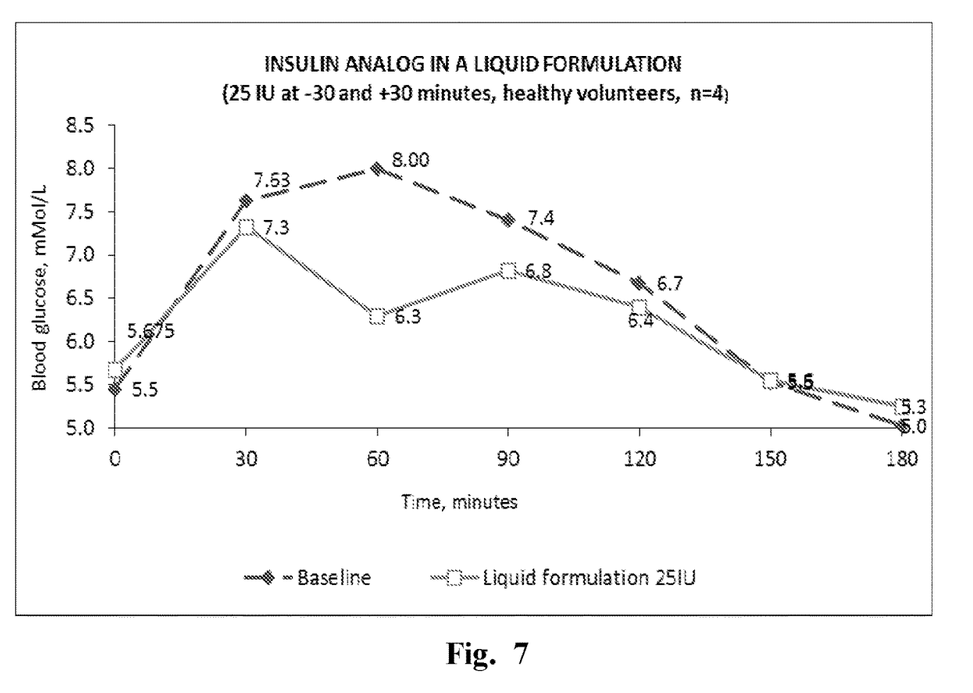
FIG. 7: Postprandial glucose levels in healthy volunteers after placebo or sublingual insulin analog (25 IU) in a liquid formulation containing salicylate ester.

Liquid compositions with insulin and insulin analogs, containing salicylate esters, also demonstrates pronounced glucose lowering activity after sublingual or buccal administration (FIG. 7).

What is claimed:

1. A solid pharmaceutical dosage form, comprising:

a. about 1.1 mg to about 2.2 mg human recombinant insulin, insulin from an animal source, plant origin insulin, modified insulin, or one or more insulin analogs;

b. about 7.5 mg to about 30 mg of a physiologically acceptable polyethoxylated surfactant or mixture of polyethoxylated surfactants;

c. about 0.8 mg to about 10 mg of dimyristoylphosphatidylglycerol (DMPG);

d. about 6 mg to about 10 mg of methyl salicylate;

e. about 5 mg to about 15 mg of lecithin;

f. about 1.2 mg to about 5 mg of menthol;

g. about 2 to about 12 mg of physiologically acceptable triglyceride, selected from the group of medium chain triglycerides or mixtures thereof; and h. about 2 to about 5 mg of tocopherol acetate.

2. The solid pharmaceutical dosage form of claim 1, wherein upon intraoral administration, the composition forms an emulsion upon contact with saliva or a water-containing medium and wherein the insulin or insulin analog(s) remains dissolved in the oil phase of the formed emulsion.

3. The solid pharmaceutical dosage form of claim 1, further comprising tocopherol acid succinate.

4. The solid pharmaceutical dosage form of claim 1, further comprising polyvinylpyrrolidone (PVP).

5. The solid pharmaceutical dosage form of claim 1, further comprising acetic acid.

6. The solid pharmaceutical dosage form of claim 1, further comprising sucralose.

7. The solid pharmaceutical dosage form of claim 1, wherein the dosage form is selected from the group consisting of a sublingual tablet, lozenge, buccal film, compressed tablet, chewable tablet, molded tablet, extruded tablet, capsule, granulation, and extruded or spheronized granulation or powder.

* * * * *